United States Patent [19]

Swenson

[11] 4,064,873
[45] Dec. 27, 1977

[54] TONGUE BLADE FOR MOUTH GAG

[76] Inventor: Rudolph E. Swenson, 3142 Windsor Court, Lafayette, Calif. 94549

[21] Appl. No.: 694,541

[22] Filed: June 10, 1976

[51] Int. Cl.² ............................................. A61B 1/00
[52] U.S. Cl. ...................................................... 128/12
[58] Field of Search ...................... 128/12, 15, 13, 14, 128/215

[56] References Cited

U.S. PATENT DOCUMENTS

| | | | |
|---|---|---|---|
| 1,193,782 | 8/1916 | Henderson | 128/15 |
| 1,319,904 | 10/1919 | Roberts | 128/12 |
| 2,476,675 | 7/1949 | McIvor | 128/12 |
| 2,756,742 | 7/1956 | Barton | 128/15 |
| 4,024,859 | 5/1977 | Slepyan et al. | 128/12 |

OTHER PUBLICATIONS

Catalog of V. Mueller & Co., Chicago, 1938, p. 119.

*Primary Examiner*—Stephen C. Pellegrino
*Assistant Examiner*—Henry S. Layton

[57] ABSTRACT

An improved tongue blade that may be used with frames of conventional design and forming part of a mouth gag, said blade having a handle portion that connects with a frame and a tongue-engaging portion that extends from said handle portion at an obtuse angle of between 120° and 135°, said blade providing an improved exposure of the tonsils for surgical removal. The improved exposure is uniquely attained in the lower pole for more complete removal of the tonsil, and easier access to bleeding vessels for quicker ligation of bleeders.

6 Claims, 5 Drawing Figures

TONGUE BLADE FOR MOUTH GAG

This invention relates generally to mouth gags and more particularly to an improved tongue blade for use with frames or holders of conventional design. As compared with tongue blades of the existing art, the improved tongue blade of this invention, permits much wider opening of the mouth at the level of the incisor teeth while simultaneously applying less pressure at the level of the tonsillar pillars and soft palate, and this is accomplished without unduly stretching the temporomandibular joint. As a consequence, the relaxed soft palate is more easily retracted to allow better vision of the naso-pharynx, as well as easier access to the adenoids for purposes of surgical removal. Relaxed tonsillar pillars also facilitate the dissection of the tonsils and provide a better view of the lower pole. In addition, better exposure and access facilitates the ligation of bleeders.

Prior art tongue blades essentially consist of a curved tongue-engaging portion that connects to a handle at approximately a right angle; and in many instances the tongue-engaging portion actually connects at an acute angle. The tongue blades of the present invention, however, are formed with tongue-engaging portions comprising an essentially straight section that projects from the handle at an obtuse angle which may vary between 120° and 135°. The obtuse angular connection coacts synergistically with a curved tip formed on a radius of curvature less than ¾ inch to provide a localized pressure directly in front of the lingual tonsil. The resultant effect is materially different from the pressure contact and performance afforded by prior art tongue blades which stretch the temporomandibular joint by applying pressure largely in the region of the tonsillar pillars and soft palate.

Thus, a principal object of the present invention is to provide an improved tongue blade that is adapted for use with most conventional frames for a mouth gag.

In the drawings, forming a part of this application, and in which like parts are identified by like reference numerals throughout the same, FIG. 1 is a perspective view of a mouth gag comprising a conventional frame and a tongue blade formed in accordance with the present invention;

Figure 1:
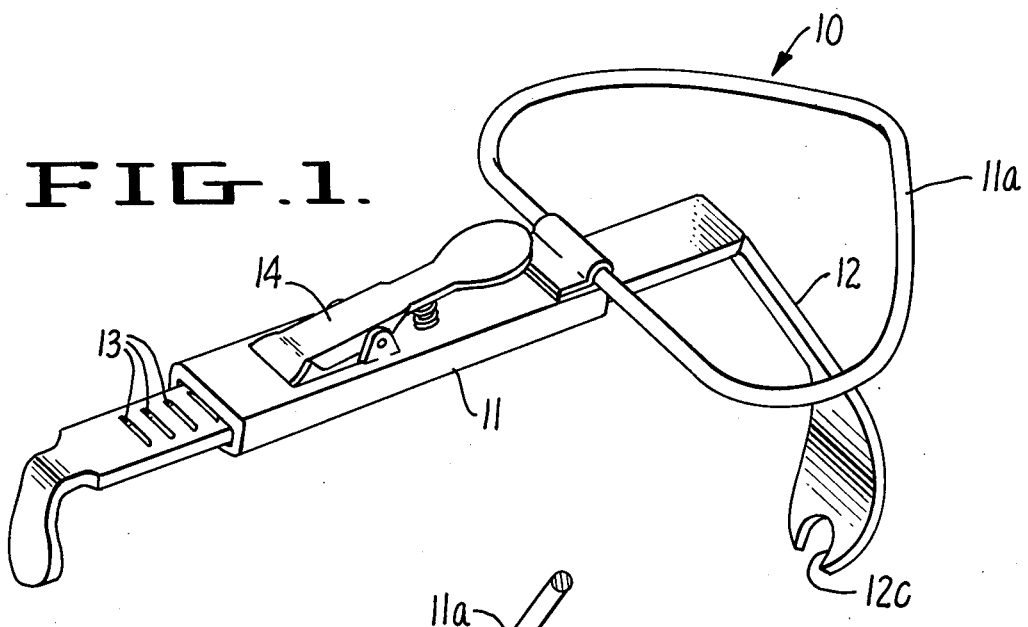
Figure 2:
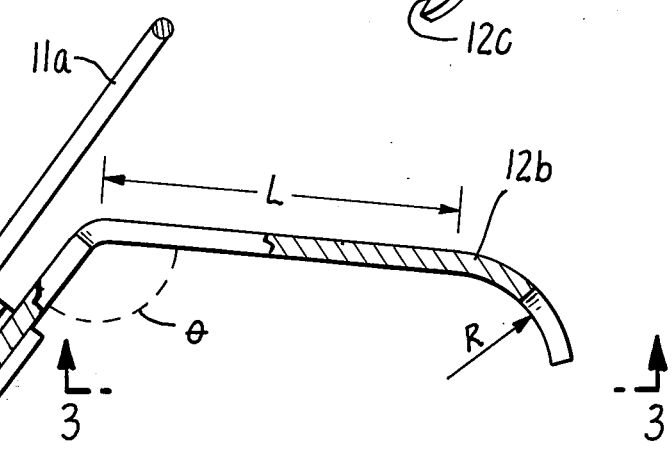
FIG. 2 is a side view of the mouth gag, a portion of the tongue blade being shown in center section.
Figure 3:
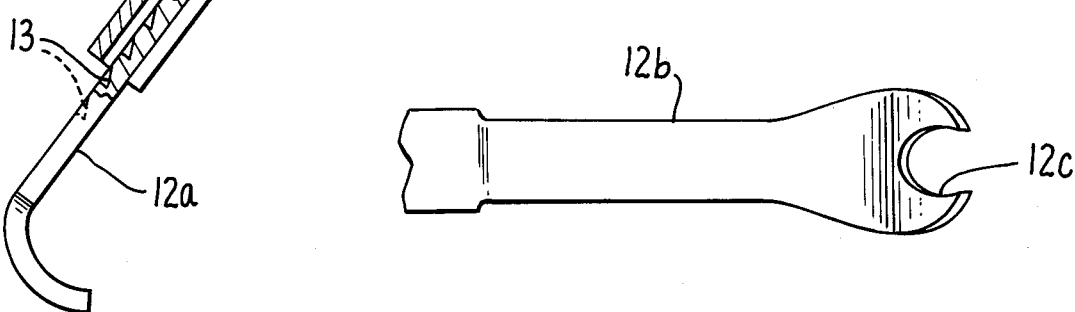
FIG. 3 is a bottom plan view of a portion of the tongue blade as viewed on the lines 3–3 of FIG. 2.

Referring to FIG. 1, there is illustrated a mouth gag 10 comprising a frame 11, including a forward projecting rod 11a that engages the upper teeth, and a tongue blade 12. Frame 11 is conventional in construction and is commonly known as a McIvor frame. Tongue blade 12, however, as in FIGS. 2 and 3, is made in accordance with the teaching of this invention and comprises a handle 12a and a tongue-engaging portion 12b consisting of an essentially straight section and a curved tip which has a semicircular opening 12c to guide the endotracheal tube for anesthesia. A rack-like surface is formed on one side of handle 12a by a plurality of grooves 13 which are engaged by a pawl 14 pivotally connected to frame 11. This structural detail is conventional to the McIvor frame and serves merely to adjustably position the tongue blade relative to the frame.

Figure 4:
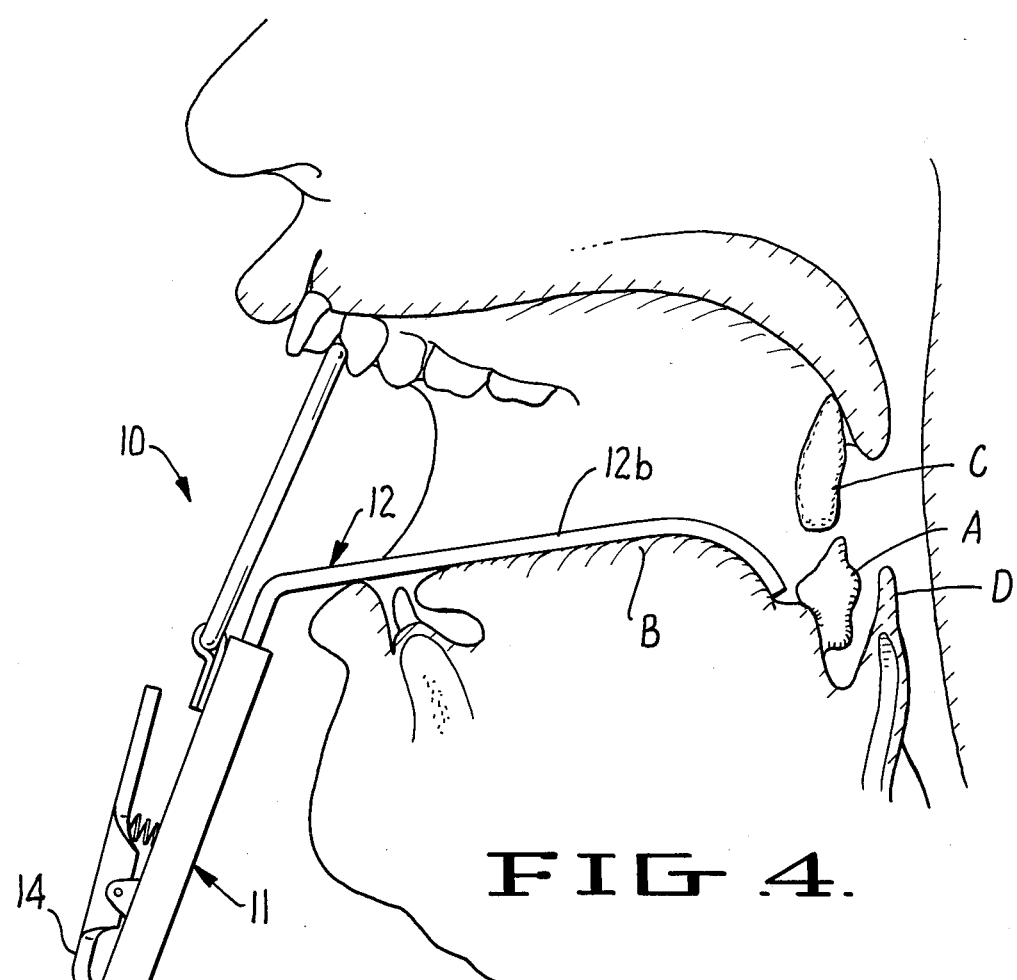
FIG. 4 is a side elevation of the mouth gag inserted in the mouth of a patient, and showing the position of the tongue blade and pressure contact.
Figure 5:
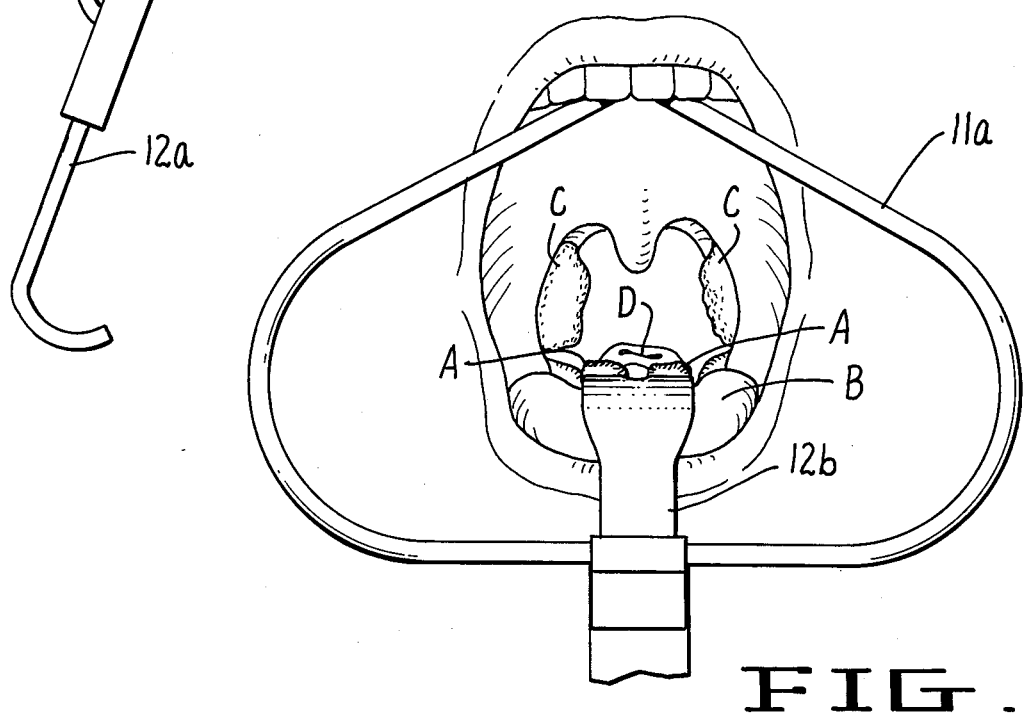
FIG. 5 is a front view looking into the mouth of the patient with the mouth gag in place.

The present invention is more particularly directed to the angular extension, shape and length of tongue-engaging portion 12b. Referring to FIG. 2 in particular, it will be noted that tongue-engaging portion 12b extends from the handle 12a at an obtuse angle $\theta$. In addition, the tongue-engaging portion possesses a curved tip formed with a radius of curvature R at a distance L from handle portion 12a. The relationship of angle $\theta$, the distance L and the curvature R are selected (depending on the mouth size and mouth configuration of the patient) to apply a pressure contact directly in front of the lingual tonsil A, as shown in FIGS. 4 and 5. It has been empirically determined that angle $\theta$ may vary between 120° and 135°; that the dimension L must be at least 2 inches in length; and that the radius of curvature R must be less than ¾ inch. Tongue blades for very small children may be formed with a curved tip having a radius of curvature as little as ½ inch.

As indicated above, the exact configuration and dimensions of the blade may vary from patient to patient. For example, the size of tongue blades suitable for use on small children would be much smaller than those for grown adults. Accordingly, a series of tongue blades should be provided for use in combination with a single frame. Because of size differences, the overall length of the tongue-engaging portion of the blade may vary between 2¾ inches and 4 inches while the dimension L varies between 2 and 3 inches in length. The curved tip of the blade may also vary depending on size. It has been empirically determined that best results will be obtained if the tip is between three-fourths inch and one inch in length.

In operation, when the curved tip of tongue blade 12 is placed directly in front of lingual tonsils A, a slight pressure on the tongue B will cause the lingual tonsils to protrude upward bringing the lingual tonsils into excellent view while fully exposing the faucial tonsils C and epiglottis D. Thus, even the rarely required lingual tonsillectomy can be accomplished with excellent access and direct vision. It will be apparent that the novel shape of the tongue blade also permits a wider opening of a small mouth without increasing the pressure on the tongue or the teeth and without damaging the temporomandibular joint. This is of particular value to plastic surgeons doing repair of cleft palates in infants, the ideal age being 18 months.

Although a preferred embodiment of the invention has been illustrated and described, various types of frame holders may be used as well as other modifications and changes without departing from the spirit of the invention or the scope of the appended claims, and each of such modifications or changes is contemplated.

What is claimed is:

1. A series of tongue blades for use in combination with a frame and forming part of a mouth gag, said tongue blades being formed in various sizes, each blade having a handle portion and a tongue-engaging portion that extends from said handle portion at an obtuse angle between 120° and 135°, said tongue-engaging portion having a curved tip that is formed with a radius of curvature less than three-fourths inch at a distance greater than 2 inches from said handle portion whereby the handle portion and tongue-engaging portion of each tongue blade define an unobstructed obtuse angular void therebetween extending from the handle portion a distance of at least 2 inches.

2. An improved tongue blade for use with a frame and forming part of a mouth gag, said blade having a handle portion that connects with a frame and a tongue-engaging portion that extends from said handle portion at an obtuse angle of between 120° and 135°, said tongue-engaging portion having an essentially straight section and a curved tip, said essentially straight section being at least 2 inches in length, said curved tip having a radius of curvature less than three-fourths inch, said handle portion and tongue-engaging portion defining an unobstructed obtuse angular void therebetween that extends from the handle portion a distance of at least 2 inches.

3. The tongue blade of claim 2, said tongue-engaging portion of said blade having an overall length of between 2 ¾ inches and 4 inches.

4. The tongue blade of claim 2, the essentially straight section of said blade being greater than 2 inches and less than 3 inches in length.

5. The tongue blade of claim 2, the curved tip of said blade being between three-fourths inch and 1 inch in length.

6. The tongue blade of claim 2, the curved tip of said blade having a radius of curvature equal to or greater than one-half inch in length.

* * * * *